United States Patent [19]

Cichanowicz et al.

[11] Patent Number: 4,885,239

[45] Date of Patent: Dec. 5, 1989

[54] RAPID DIFFERENTIATION OF BACTERIA USING POLYETHER ANTIBIOTICS

[75] Inventors: Peggy W. Cichanowicz, Pittsford; Robert T. Belly, Webster, both of N.Y.

[73] Assignee: Eastman Kodak Company, Rochester, N.Y.

[21] Appl. No.: 910,917

[22] Filed: Sep. 24, 1986

[51] Int. Cl.$^4$ .............................................. C12Q 1/04
[52] U.S. Cl. ..................................... 435/34; 435/29; 435/31; 435/38; 435/39; 435/805; 435/810
[58] Field of Search ..................... 435/29, 31, 34, 39, 435/38, 805, 810

[56] References Cited

U.S. PATENT DOCUMENTS

| | | | |
|---|---|---|---|
| 3,923,823 | 12/1975 | Gale et al. | 260/299 |
| 4,525,453 | 6/1985 | Guardino et al. | 435/34 |
| 4,746,607 | 5/1988 | Mura et al. | 435/25 |

OTHER PUBLICATIONS

Finegold et al., "Bailey and Scott's Diagnostic Microbiology" 5th Ed. C. V. Mosby Co., St. Louis, 1978, p. 21.
Westley "Polyether Antibiotics" Marcel Dekker Inc., New York, 1982, pp. 1–51.

*Primary Examiner*—Robert Benson
*Attorney, Agent, or Firm*—J. Lanny Tucker

[57] ABSTRACT

Rapid differentiation between viable gram-positive and gram-negative bacteria is accomplished with polyether antibiotics which are used in combination with a compound which is normally reducible by the bacteria. The antibiotics selectively and substantially inhibit the reduction of the reducible compound by gram-positive bacteria but do not substantially affect the reducing capacity of the gram-negative bacteria.

20 Claims, No Drawings

RAPID DIFFERENTIATION OF BACTERIA USING POLYETHER ANTIBIOTICS

FIELD OF THE INVENTION

The present invention relates to clinical chemistry. It particularly relates to a composition, element and method for differentiation between viable gram-positive and viable gram-negative bacteria.

BACKGROUND OF THE INVENTION

All bacteria can be separated into one or two classes, either gram-positive or gram-negative, based on their gram-stain reaction. The gram reaction is, therefore, a key test in the identification of bacteria. In addition, because of general structural and chemical differences between gram-positive and gram-negative bacteria, a different spectrum of antibiotics is used to treat infections caused by one class than is used to treat infections caused by the other class. Knowledge of the gram reaction of an infecting organism is, therefore, important for determination of appropriate treatment.

Currently, the gram stain reaction is a four-step staining procedure performed on a glass slide containing heat-fixed biological specimens. This procedure is both time consuming and labor intensive. Bartholomew (*The Gram Stain, Bact. Rev.*, 16, pp. 1-29, 1952) has written a comprehensive article describing this procedure. It is well known that gram staining can give varying results and is highly dependent upon precise timing and meticulous technique. Furthermore, the procedure is difficult to automate.

An improved differentiation method using anionic surfactants is described in U.S. Pat. No. 4,525,453 (issued Jun. 25, 1985). According to that reference, anionic surfactants selectively inhibit the ability of gram-positive organisms to reduce certain reducible compounds. One of the surfactants taught as preferred in that reference is marketed under the trademark TERGITOL 7 (Sigma Chemical Co., St. Louis, MO.)

It has been found, however, that the anionic surfactants taught in the art do not effectively differentiate organisms with a wide range of reducible compounds. For example, TERGITOL 7 is useful with tetrazolium salts, but is not useful with certain reducible intramolecular nucleophilic displacement compounds (identified as RIND compounds herein). In other words, no clear gram separation was observed using a combination of the anionic surfactants and the RIND compounds.

It would be desirable to have a differentiation method which is not only rapid and simple, but also would be useful with a broad range of reducible materials.

SUMMARY OF THE INVENTION

The problems noted above with known differentiation procedures are avoided with a composition for differentiating between viable gram-positive and gram-negative bacteria comprising:

(a) a compound capable of being reduced to a detectable species by both viable gram-positive and gram-negative bacteria in the absence of reduction-inhibiting materials, and (b) a polyether antibiotic present in an amount sufficient to selectively and substantially inhibit the reduction of the reducible compound by the gram-positive bacteria.

The present invention also provides an analytical element for differentiating between viable gram-positive and gram-negative bacteria comprising an absorbent carrier material and containing:

(a) a compound capable of being reduced to a detectable species by both viable gram-positive and gram-negative bacteria in the absence of reduction-inhibiting materials, and (b) a polyether antibiotic present in an amount sufficient to selectively and substantially inhibit the reduction of the reducible compound by the gram-positive bacteria.

Further, a method for differentiating between viable gram-positive and gram-negative bacteria comprises the steps of:

A. mixing a liquid suspected of containing viable gram-positive and gram-negative bacteria with (a) a compound capable of being reduced to a detectable species by both viable gram-positive and gram-negative bacteria in the absence of reduction-inhibiting materials, and (b) a polyether antibiotic present in an amount sufficient to selectively and substantially inhibit the reduction of the reducible compound by gram-positive bacteria, and B. determining the detectable species resulting from the presence of the gram-negative bacteria.

The present invention provides a rapid, simple and relatively inexpensive means for differentiating the gram type of viable bacteria. This invention avoids the undesirable tedious features of standard gram stain techniques. Further, a wide variety of reducible compounds can be used thereby giving greater flexibility in the assay. For example, such flexibility allows the use of dyes which have high sensitivity, are less toxic to bacteria or which can be detected in spectral regions not affected by potential interferents found in biological fluids.

These advantages are achieved by using polyether antibiotics in combination with a compound which can be reduced by the bacteria in the absence of reduction-inhibiting materials. The antibiotic selectively and substantially inhibits the reducing capacity of gram-positive bacteria while the capacity of gram-negative bacteria is substantially unaffected.

DETAILED DESCRIPTION OF THE INVENTION

The antibiotics useful in the practice of this invention are those known in the art as polyether antibiotics. Such materials are described in more detail in a text edited by J. W. Westley entitled *Polyether Antibiotics*, Vol. 1, Marcel Dekker, Inc., N. Y., 1982, e.g. at page 6. Polyether antibiotics are generally understood to be antibiotics having a multiplicity (two or more) of cyclic ether groups.

According to the Westley reference noted above, polyether antibiotics have been divided into several classes, all of which are useful in the practice of the present invention. Without intending to be so limited in the practice of this invention, these classes, along with representative antibiotics are listed in Table I below.

TABLE I

| Class | Representative Antibiotics |
|---|---|
| 1a: Monovalent | Alborixin (S 14750A) |
| | Antibiotic X-206 |
| | Grisorixin |
| | Laidlomycin |
| | Monensin A |

TABLE I-continued

| Class | Representative Antibiotics |
|---|---|
| | Nigericin (X-464, polyetherin A, azalomycin M, duamycin, K 178) |
| | Salinomycin |
| | Salinomycin SY-4 (5-hydroxy) |
| 1b: Monovalent Glycoside | Antibiotic A204 |
| | Carriomycin (T-42082) |
| | Etheromycin (CP 38295, C20-12) |
| | Septamycin (A28695A, B1-580α) |
| 2a: Divalent | Ionomycin |
| | Lasalocid A(X-537A) |
| | Lasalocid B |
| | Lasalocid C |
| | Lasalocid D |
| | Lysocellin (X-14537) |
| 2b: Divalent Glycoside | Antibiotic 6016 |
| 3: Divalent Pyrrole Ether | Antibiotic A23187 (Calimycin or Calcimycin) |
| | Antibiotic X-14547A |

Calimycin (also known as Antibiotic A23187), monensin, ionomycin, Antibiotic A204, septamycin (also known as A28695A) and the lasalocid antibiotics are preferred in the practice of this invention. As is known in the art, calimycin, ionomycin and septamycin are used in combination with calcium ions for optimal activity.

It will be understood by those skilled in the art that for each antibiotic useful in the present invention there will be an optimal concentration range (depending upon the purity and potency of the antibiotic) and optimal environmental conditions for substantially inhibiting the reductive capability of gram-positive bacteria and for differentiation. Further, there may be a few exceptions to the selective inhibitory action of the polyether antibiotics to certain gram-positive bacteria. However, the classes of polyether antibiotics generally exhibit the selective substantial inhibition described herein.

In general, the amount of antibiotic needed to selectively and substantially inhibit the reduction of the reducible compound (described below) by gram-positive bacteria can be determined readily by mixing about $10^7$ cells/ml of a gram-positive bacterium (for example, $S.$ $aureus$), an antibiotic (about $10^{-4}$ molar) and a reducible compound (about 0.005 molar) at pH 7.5. If the reducible compound is reduced thereby producing a detectable change, the amount of antibiotic is increased accordingly in further tests until no detectable change is observed.

The reducible compound useful in the practice of this invention can be any material that, in its oxidized form, is capable of being reduced by both viable gram-positive and gram-negative bacteria, in the absence of any reduction-inhibiting materials, to produce a detectable species. Such species can be detected by any suitable means including potentiometric or radiometric means. Preferably, as defined below, the species is detected with radiometric means.

A partial listing of various detectable species that are directly detectable by radiometric means includes colorimetrically detectable materials, such as chromogens, radiation emission materials, such as fluorogens, chemiluminescent materials, radioactive isotopes, phosphorescent materials, etc.

The use of dyes or dye precursors as the detectable species is preferred. The use of dyes or dye precursors presents several possibilities for detection: (1) a colored species can become colorless or undergo a shift in absorption, (2) a colorless species, that is, a dye precursor can form a colored species, or (3) a species containing a shiftable detectable species can release the shiftable detectable species. Alternative (3) is preferred in the practice of this invention.

Examples of dyes or dye precursors that can be used as reducible compounds include methylene blue, dichloroindophenol, resazurin, and various tetrazolium compounds, such as 3-(4,5-dimethyl-2-thiazolyl)-2,5-diphenyl-2H-tetrazolium bromide, 2,3,5-triphenyl-2H-tetrazolium chloride, tetranitro blue, tetrazolium chloride and nitrotetrazolium violet, and others described, for example in U.S. Pat. No. 4,525,453, noted above.

More particularly, the reducible compounds useful in this invention have the structure CAR$(R^1)_n$ wherein CAR—represents a substituted or unsubstituted aromatic or quinone nucleus, $R^1$ is a moiety comprising a shiftable detectable species defined herein, and n is 1 or 2. The term "shiftable detectable species" can be defined as a chromogen moiety which has a first spectral absorption band when attached to the reducible compound and a second absorption band when released from the reducible compound, or a fluorogen moiety which has first spectral absorption and emission bands when attached to the reducible compound and second spectral absorption and emission bands when released. Examples of such nuclei are presented below. Further, when $R_1$ is replaced by H, CAR$(H)_n$ has a reduction potential ($E_{\frac{1}{2}}$) of either at least about +100 mV when measured in water, or of at least about −650 mV when measured in acetonitrile. This $E_{\frac{1}{2}}$ value facilitates the reduction and subsequent release of the detectable species from the compound at physiological pH (that is, 9 or less). Such measurements are made according to standard electrochemical techniques using either differential pulse polarography or cyclic voltametry (see, for example, Sawyer and Roberts, Jr., *Experimental Electrochemistry for Chemists*, John Wiley & Sons, N.Y., 1974). Preferably, the $E_{\frac{1}{2}}$ is from about +100 mV to about +400 mV as measured in water, or from about −650 to about −300 mV as measured in acetonitrile. Both ranges are given because some of the reducible compounds are best measured in water whereas others are best measured in acetonitrile. Further details of measuring the $E_{\frac{1}{2}}$ are described below prior to Table I. The desired $E_{\frac{1}{2}}$ is achieved by appropriate electron withdrawing groups on the CAR—nucleus, or by a strained fused ring attached to the nucleus or a combination of both.

In one embodiment, the reducible compounds can be reduced to provide a detectable species through quinone methide formation, similar to the description by Van de Sande in *Angew. Chem. Int. Ed. Engl.* 22, pp. 191–209 (1983) and U.S. Pat. No. 4,232,107 (issued Nov. 4, 1980 to Janssens), but which have the desired $E_{\frac{1}{2}}$ properties.

In another embodiment, useful reducible compounds include sulfilimides and sulfenylsulfonamides similar to those described on page 206 of the Van de Sande reference noted above, but which have the desired $E_{\frac{1}{2}}$ properties.

In a preferred embodiment, the reducible compounds are RIND compounds, that is, reducible compounds capable of undergoing intramolecular nucleophilic displacement at physiological pH to release one or more detectable species when a nucleophilic group is generated by at least a one electron reduction of the compound. In other words, such displacement occurs when the RIND compound is reduced by a suitable reductant which provides the necessary electron(s) (described in more detail below). The release of detectable species is very efficient in that, for most of the preferred compounds, at least 50% of the detectable species is provided within 30 minutes at about pH 7.

The term "intramolecular nucleophilic displacement" refers to a reaction in which a nucleophilic center on a molecule reacts at another site in the molecule, which site is an electrophilic center, to effect displacement of a group or atom attached to the electrophilic center. Generally, the RIND compounds useful in this invention have the nucleophilic and electrophilic groups juxtaposed in the three-dimensional configuration of the molecule in close proximity whereby the intramolecular reaction can take place and a ring is formed having from 4 to 7 atoms, and preferably having 5 or 6 atoms.

Particularly useful RIND compounds are those represented by the structure CAR—$R^1$ wherein CAR— is

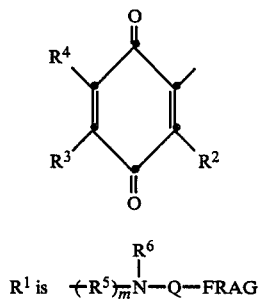

$R^1$ is $+R^5)_{\overline{m}}N-Q-FRAG$ wherein m is 0 or 1, and preferably 1. $R^5$ is substituted or unsubstituted alkylene, preferably of 1 or 2 carbon atoms in the backbone (for example, methylene, ethylene or alkoxymethylene). Most preferably, $R^5$ is methylene. Q is carbonyl or thiocarbonyl and preferably carbonyl.

$R^6$ is substituted or unsubstituted alkyl, preferably of 1 to 40 carbon atoms (for example, methyl, ethyl, n-propyl, isopropyl, t-butyl, hexyl, decyl, lauryl, benzyl or n-propyl-n-butylether), substituted or unsubstituted cycloalkyl, preferably of 4 to 40 carbon atoms (for example, cyclobutyl, cyclohexyl or 4-methylcyclohexyl), substituted or unsubstituted heterocycle, preferably of 5 to 40 atoms (carbon and heteroatoms, for example, pyridyl), or substituted or unsubstituted aryl, preferably of 6 to 40 carbon atoms (for example, phenyl, xylyl, naphthyl, p-nitrophenyl, anthryl, p-t-butoxyphenyl or p-carboxyphenyl). Preferably, $R^6$ is substituted or unsubstituted alkyl or substituted or unsubstituted aryl as defined above.

FRAG is a shiftable detectable species as defined above. The specific composition of FRAG can vary considerably depending upon the type of detectable species desired and upon the particular detection means employed. The detectable species can be a material which is directly detectable by a suitable means, as well as a material which can react with other substances, for example, analytes, enzymes or other reagents to provide a detectable species.

Particularly useful detectable species are chromogens and fluorogens. Examples of useful classes of chromogens are azo, azomethine, nitrophenol, indophenol, indoaniline and triarylmethane dyes, and others known in the art, with azo dyes being preferred. Examples of useful classes of fluorogens are coumarin, umbelliferone, phenalenone and benzphenalenone, 4-oxo-4-H-benz-[d,e]anthracenes, fluorescein and rhodamine fluorescent dyes, and others known in the art. Phenalenone dyes are particularly useful.

Useful phosphorescent species include such phosphors as 2',5'-dibromofluorescein and 4',5'-diiodofluorescein. A useful chemiluminescent species is luciferin.

FRAG is linked to Q by means of a single bond through a bivalent monoatom linkage which is a part of FRAG. Preferably, the monoatom linkage is oxy, thio or seleno when FRAG is a chromogen and oxy or thio when FRAG is a fluorogen. Most preferably, the linkage is oxy.

$R^2$, $R^3$ and $R^4$ in the above quinone structure are independently hydrogen, substituted or unsubstituted alkyl of 1 to 40 carbon atoms (for example, methyl, ethyl, hydroxymethyl or methoxymethyl) substituted or unsubstituted aryl (for example, phenyl, naphthyl, methylnaphthyl, p-nitrophenyl, m-methoxyphenyl or p-carboxyphenyl) or an electron withdrawing group which generally has a positive Hammett sigma value, and preferably has a sigma value greater than about 0.06. At least one of $R^2$, $R^3$ and $R^4$ is an electron withdrawing group. Hammett sigma values are calculated in accordance with standard procedures described, for example, in *Steric Effects in Organic Chemistry*, John Wiley & Sons, Inc., 1956, pp. 570–574 and *Progress in Physical Organic Chemistry*, Vol. 2, Interscience Publishers, 1964, pp. 333–339. Representative electron withdrawing groups having positive Hammett sigma values include cyano, carboxy, nitro, halo (for example, fluoro, bromo, chloro or iodo), trihalomethyl (for example, trifluoromethyl or trichloromethyl), trialkylammonium, carbonyl, carbamoyl, sulfonyl, sulfamoyl, esters and others known in the art, or alkyl or aryl groups (defined above) substituted with one or more of these electron withdrawing groups. Preferred electron withdrawing groups include p-nitrophenyl, m-nitrophenyl, p-cyanophenyl and 2,5-dichlorophenyl. Aryl groups with methoxy or acetamido groups in the meta position are also useful.

$R^3$ can also be $R^1$ thereby potentially providing a 2:1 molar ratio of detectable species molecules to original RIND compound molecules.

Alternatively, $R^3$ and $R^4$, taken together, can represent the carbon atoms necessary to complete a substituted or unsubstituted strained fused carbocyclic ring attached to the quinone nucleus. Strained fused rings are known in the art (for example, Rieke et al, *Tetrahedron Letters*, 50, pp. 4381–4384, 1969). For example, such a ring (mono- or bicyclic) can have from 4 to 8 carbon atoms in the backbone. Preferably, the ring is a 5-membered mono-ring, or a 7- or 8-membered bicyclic ring.

Particularly useful reducible compounds are those described and claimed in copending and commonly assigned U.S. Ser. No. 868,855, filed May 30, 1986, by Mura et al and entitled WATER-COMPATIBLE REDUCIBLE COMPOUNDS AND THEIR USE IN ANALYTICAL COMPOSITIONS AND METHODS.

Representative RIND compounds are listed in Table II below in reference to the following structure:

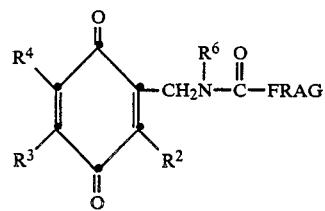

The $E_{\frac{1}{2}}$ values in Table II were determined for the quinone nucleus of this structure having a hydrogen atom in place of

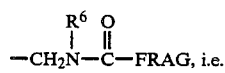

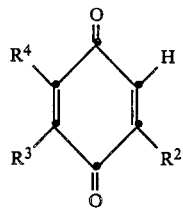

The $E_{\frac{1}{2}}$ values (where available) were measured in an aqueous emulsion of the quinone dissolved in N,N-dimethylformamide, a nonionic surfactant (TRITON X-100) and sodium phosphate buffer (pH 7). A standard calomel electrode was used as a standard. Some $E_{\frac{1}{2}}$ values (denoted by *) were measured in acetonitrile using a saturated calomel electrode as a standard. $E_{\frac{1}{2}}$ values not available are denoted by "NA".

TABLE II

| RIND Compound | R⁶ | R² | R⁴ | R³ | FRAG | $E_{\frac{1}{2}}$ (mV) |
|---|---|---|---|---|---|---|
| I. | —CH₃ | —CH(CH₃)(C₆H₄-SO₂NHC₁₀H₂₁) | same as R² | —CH₂N(CH₃)—C(O)—FRAG | (naphthalene with —O⁻, N=N-phenyl(SO₂CH₃)(NO₂), NHSO₂-phenyl-SO₂NH₂) | −528* |
| II. | —CH₃ | —CH(CH₃)(C₆H₄-NO₂) | " | " | " | +236 |
| III. | —CH₃ | —CH(CH₃)(C₆H₄-SO₂NHCH(CH₃)₂) | " | " | " | NA |
| IV. | —CH₃ | —C₆H₅ | " | " | " | −460* |
| V. | —CH₃ | —C₆H₄-NO₂ | R³ and R⁴ together form | | " | +214 |
| VI. | —CH₃ | —C₆H₅ | " (phenyl ring fused) | " | " | +180 |

TABLE II-continued

| RIND Compound | R⁶ | R² | R⁴ | R³ | FRAG | E₁ (mV) |
|---|---|---|---|---|---|---|
| VII. | —CH₃ | 4-NO₂-C₆H₄— | | " | " | +236 |
| VIII. | —CH₃ | 4-SO₂NHCH(CH₃)₂-C₆H₄— | | " | " | +212 |
| IX. | —CH₃ | 4-CN-C₆H₄— | | " | " | +220 |
| X. | —CH₃ | 4-OCH₃-C₆H₄— | | " | " | +154 |
| XI. | —CH₃ | 3,5-(NO₂)₂-C₆H₃— | | " | " | +186 |
| XII. | —CH₃ | 4-C(=O)C₁₀H₂₁-C₆H₄— | | " | " | +206 |
| XIII. | —CH₃ | 4-C(=O)CH₃-C₆H₄— | | " | " | +212 |

TABLE II-continued

| RIND Compound | R⁶ | R² | | R⁴ | R³ | FRAG | $E_{\frac{1}{2}}$ (mV) |
|---|---|---|---|---|---|---|---|
| XIV. | —CH₃ | 4-Br-phenyl | | | " | " | +192 |
| XV. | —CH₃ | —H | | | " | " | +213 |
| XVI. | —C₁₂H₂₅ | 4-CN-phenyl | | " | " | " | +220 |
| XVII. | —CH₃ | " | | R³ and R⁴ together form cyclohexene | | " | +240 |
| XVIII. | —CH₃ | 4-NO₂-phenyl | | —t-butyl | —H | " | NA |
| XIX. | —CH₃ | phenyl | | R³ and R⁴ together form | | " | +242 |
| XX. | —CH₃ | " | | R³ and R⁴ together form | | " | +222 |

TABLE II-continued

| RIND Compound | R⁶ | R² | R⁴ | R³ | FRAG | E₁ (mV) |
|---|---|---|---|---|---|---|
| XXI. | —CH₃ | 4-(SO₂NHC₁₀H₂₁)-phenyl with α-CH(CH₃)— | same as R² | —CH₂N(CH₃)—C(=O)—FRAG | 4-methoxy-naphthyl with 1-(3-SO₂NH₂-phenylazo), 8-NHSO₂CH₃ | −528* |
| XXII. | —CH₃ | " | " | " | 4-methoxy-2-methylphenyl acrylate (lactone) | −528* |
| XXIII. | —CH₃ | 4-NO₂-phenyl | R³ and R⁴ together form (ring) | | " | +214 |
| XXIV | —CH₃ | 2,4-diCl-phenyl | R³ and R⁴ together form (ring) | | 4-methoxy-naphthyl with 1-(2-SO₂CH₃-4-NO₂-phenylazo), 8-NHSO₂-(3-SO₂NH₂-phenyl) | +236 |
| XXV. | —CH₃ | —phenyl | R³ and R⁴ together form C₁₂H₂₅ branched | | " | +222 |

TABLE II-continued

| RIND Compound | R$^6$ | R$^2$ | R$^4$ | R$^3$ | FRAG | E$_{\frac{1}{2}}$ (mV) |
|---|---|---|---|---|---|---|
| XXVI. | —CH$_3$ | " | —CH$_3$ | —CH$_3$ | " | +144 |
| XXVII. | —CH$_3$ | " | | | " | +122 |
| XXVIII. | —CH$_3$ | " | R$^3$ and R$^4$ together form (CH$_3$)$_2$HC—, CH$_3$ (cyclohexane) | | " | +174 |
| XXIX. | —CH$_3$ | (4-CN-phenyl) | R$^3$ and R$^4$ together form (cyclohexene) | | (perinaphthenone-O—) | +220 |
| XXX. | —CH$_3$ | (phenyl) | R$^3$ and R$^4$ together form (cyclopentane) | | " | +222 |
| XXXI. | —CH$_3$ | (2,5-dichlorophenyl) | | | " | +236 |

TABLE II-continued

| RIND Compound | R⁶ | R² | R⁴ | R³ | FRAG | E₁ (mV) |
|---|---|---|---|---|---|---|
| XXXII. | —CH₃ | 4-NO₂-phenyl | R³ and R⁴ together form | | " | +214 |
| XXXIII. | —CH₃ | 4-NO₂-phenyl | | " | " | +236 |
| XXXIV. | —CH₃ | 4-SO₂NH(CH₃)₂-phenyl | | " | " | +212 |
| XXXV. | —CH₃ | 4-COOH-phenyl | | " | " | +220 |

RIND compound XXXV is preferred in the practice of this invention.

The RIND compounds useful in the practice of this invention are prepared using a sequence of individually known reactions. Generally, the preparation sequence includes the following general steps: (1) preparation of the substituted hydroquinone, (2) oxazine ring formation, (3) oxazine ring opening, (4) preparation of the carbamoyl chloride, and (5) reaction of a compound from which the FRAG moiety is derived with the carbamoyl chloride. Preparation of these compounds is described in more detail in copending and commonly assigned U.S. Ser. No. 824,766, filed Jan. 31, 1986 by Belly et al and entitled REDUCIBLE COMPOUNDS AND ANALYTICAL COMPOSITIONS, ELEMENTS AND METHODS UTILIZING SAME and in U.S. Ser. No. 868,855 of Mura et al, noted above.

Other RIND compounds useful in the practice of this invention include those having the appropriate $E_{\frac{1}{2}}$ values and the structure CAR $(R^1)_n$ wherein:

(1) CAR—is a substituted or unsubstituted nucleus of a 1,2-naphthoquinone, 1,2-, 1,4- or 9,10-anthraquinone, 4,4'-diphenoquinone, azuloquinone or 1,6-[10]-anulenoquinone wherein $R^1$ is attached to the nucleus one carbon atom distant or in the peri position from one of the oxo groups of the nucleus. The nucleus can be substituted with one or more electron withdrawing groups as described above for $R^2$ or have one or more fused rings as described above for $R^3$ and $R^4$. $R^1$ is

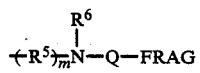

as defined above, and n is an integer of 1 or 2.

(2) CAR— is 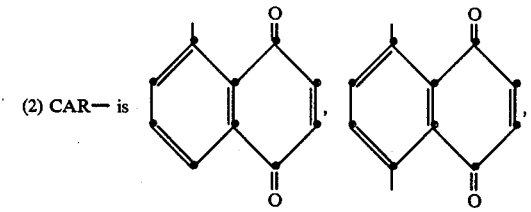, 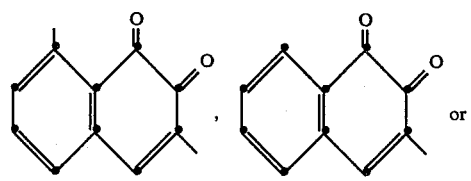, or 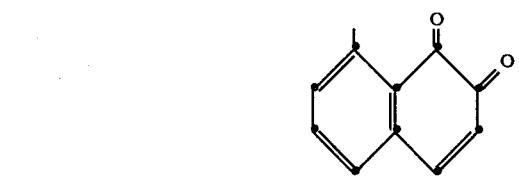

any of which can be substituted with one or more electron withdrawing groups as described above for $R^2$, $R^3$ and $R^4$. $R^1$ is

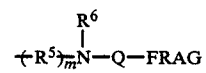

as defined above, and n is 1 or 2.

(3) CAR—is a substituted or unsubstituted nitrobenzenoid nucleus of the structure

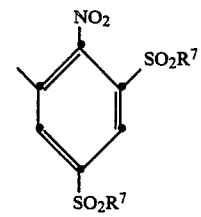

wherein $R^7$ is substituted or unsubstituted alkyl of 1 to 20 carbon atoms (for example, methyl, ethyl, methoxymethyl, isopropyl, dodecyl, hexadecyl or octadecyl), and $R^1$ is

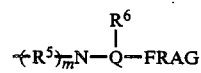

as defined above and n is 1. These compounds are similar to some described in U.S. Pat. No. 4,139,379 (noted above).

In another embodiment, the reducible compound can be a cobalt (III) complex, as described in copending and commonly assigned U.S.S.N. 890,050, filed by Schmittou Jul. 28, 1986 and entitled COBALT CONTAINING REAGENTS AND METHODS FOR THE DETERMINATION OF ANALYTES IN AQUEOUS FLUIDS.

All of these reducible compounds can be prepared using techniques and starting materials known in the art or readily apparent to a skilled synthetic chemist.

Generally, the RIND compounds described herein have limited water solubility. Hence, it is best, when using them in an aqueous environment, to prepare a dispersion of the compound prior to use, for example, in a coating formulation. Such dispersions generally comprise the reducible compound, an aqueous buffer solution and either a solubilizing surfactant or a water-miscible organic solvent for the compound, or both. Surfactants which are useful in the practice of this invention include any surfactants which do not inhibit compound reduction. Nonionic surfactants are particularly useful.

Useful water-miscible organic solvents include alcohols (for example, methanol, ethanol or propanol), N,N-dimethylformamide, dimethyl sulfoxide, acetonitrile, hexamethylenephosphoramide and the like. The particular solvent to be used for a particular reducible compound can be readily determined by routine experimentation.

A dispersion can be prepared in the following general manner. The reducible compound is dissolved in the water-miscible solvent at a concentration which depends upon its molecular weight, but generally at from about 1 to about 100, and preferably from about 5 to about 80, mg per ml of solvent. The resulting solution is then mixed with a suitable surfactant in an amount generally of from about 0.1 to about 24, and preferably from about 0.5 to about 10, ml surfactant per ml of dispersion. This preparation is generally carried out at room temperature.

When using the water-compatible reducible compounds described above, compositions containing same can be prepared without the use of surfactants. The compounds can be dissolved in an appropriate organic solvent, and the resulting solution added directly to a buffer.

The compositions of this invention generally contain a buffer in an amount effective to maintain a pH of 9 or less. The concentration of buffer in the dispersion can vary widely, but is generally from about 0.01 to about 0.1 molar. Representative buffers include phosphates, and others reported by Good et al in *Biochemistry*, 5, 467 (1966), and *Anal. Biochem.*, 104, 300 (1980).

The present invention is useful for differentiation of viable gram-positive and gram-negative bacteria in any fluid specimen including wastewater, food stuffs, manufacturing solutions and biological fluids. It is particularly useful in differentiation of bacteria in human biological fluids, such as urine, serum, whole blood, sputum, spinal fluid and other fluids known to one skilled in the art, and more particularly for those commonly found in the human urinary tract.

Differentiation of viable bacteria according to this invention is preferably carried out in the presence of an electron transfer agent (identified herein as an ETA). The presence of an ETA provides more rapid dye release. It is a mobile compound which acts as an intermediary between the microorganism and the reducible compound. An ETA is generally present at a concentration that is dependant upon the concentration of the reducible compound, but preferably at a concentration of from about $1 \times 10^{-3}$ molar to about $1 \times 10^{-7}$ molar.

ETA compounds useful in the practice of this invention include phenazine methosulfate, phenazine ethosulfate and similar compounds known to one skilled in the art. Combinations of different ETA compounds can be used if desired.

Preferred ETA compounds are those which are the subject of copending and commonly assigned U.S. Ser. No. 699,374 of Mura et al filed Feb. 7, 1985, now U.S. Pat. No. 4,746,607. In general, those compounds are substituted benzo- and naphthoquinones. Examples of this class of quinones include 2,3-dimethyl-5-hydroxymethyl-1,4-benzoquinone, 2,5-dimethoxy-1,4-benzoquinone, 2,3,5-trimethyl-1,4-benzoquinone, 2,6-dimethoxy-1,4-benzoquinone, 2,3-dimethoxy-5-methyl-1,4-benzoquinone, 2-hydroxymethyl-1,4-naphthoquinone and 2-(2-hydroxyethyl)-1,4-naphthoquinone. Substituted 1,2-benzoquinones, such as 4,5-dimethoxy-1,2-benzoquinone, are also useful in the practice of this invention.

The differentiation of viable cells is often carried out in the presence of a nutrient for those living cells although its presence is not essential. Any nutrient medium can be used which contains useful carbon, and optionally nitrogen, sources. Suitable nutrient media having proper components and pH are well known in the art.

In the method of this invention, the amount of polyether antibiotic concentration can vary widely depending upon the antibiotic and reducible compound used, as well as the particular bacteria being differentiated. However, it is generally present in an amount of at least about $10^{-5}$, and preferably from about $10^{-4}$ to about $10^{-2}$, molar. Optional materials are present in amounts which one skilled in the art can readily determine with routine experimentation.

The method of this invention can conveniently be carried out in standard laboratory glassware, for example, using test tubes, microtitration plates or slides. A liquid sample suspected of containing the bacteria are mixed with the reducible compound, polyether antibiotic and any other materials as required. After an appropriate time for microbial reaction and reduction of the reducible compound by gram-negative bacteria, the amount of detectable species resulting from reduction is measured with suitable equipment and procedures.

In some instances, it may be desirable to mix and incubate the test sample containing bacteria and the antibiotic in a pretreatment step prior to mixing with the reducible compound therein. This may reduce the amount of background density encountered with some assays due to the presence of impurities in the antibiotics. Another pretreatment to eliminate interferents may also be desirable.

The method can also be carried out by contacting a porous absorbent material, for example, paper strip, containing a test sample with a dispersion of the reducible compound and polyether antibiotic. The bacteria in the test sample can intermingle with the dispersion and initiate the analytical reactions needed for differentiation.

In one embodiment, a test strip can be used as a convenient way to carry measured amounts of reagent(s) to the test solution in a solution assay. The test strip is placed into a solution that might already contain the analyte to be measured. The reagents dissolve from the test strip into the solution so as to form the reaction solution. In preferred embodiments of the test strips of the present invention, the reagents are carried in a water soluble binder. When the test strip is immersed into the solution, the binder dissolves releasing the reagents. Useful water soluble polymers include poly(N-vinyl-2-pyrrolidone) and poly(acrylamideco-N-vinyl-2-pyrrolidone)(90:10 weight ratio).

Alternatively, the method of this invention can be practiced with a dry analytical element. Such an element can be a absorbent carrier material, that is, a thin sheet or strip of self-supporting absorbent or bibulous material, such as filter paper or strips, which contains the reducible compound and polyether antibiotic or a dried residue of same. Such elements are known in the art as test strips, diagnostic elements, dip sticks or diagnostic agents.

When employed in dry analytical elements, the reducible compounds and antibiotics described herein can be incorporated into a suitable absorbent carrier material by imbibition or impregnation, or can be coated on a suitable absorbent material. Useful carrier materials are insoluble and maintain their structural integrity when exposed to water or physiological fluids such as urine or serum. Useful carrier materials can be prepared from paper, porous particulate structures, cellulose, porous polymeric films, glass fiber or woven and nonwoven fabrics (synthetic and nonsynthetic). Useful materials and procedures for making such elements are well known in the art as exemplified by U.S. Pat. Nos. 3,092,465 (issued Jun. 4, 1963 to Adams et al), 3,802,842 (issued Apr. 9, 1974 to Lange et al), 3,915,647 (issued Oct. 28, 1975 to Wright), 3,917,453 (issued Nov. 4, 1975 to Milligan et al), 3,936,357 (issued Feb. 3, 1976 to Milligan et al), 4,248,829 (issued Feb. 3, 1981 to Kitajima et al), 4,255,384 (issued Mar. 10, 1981 Kitajima et al), and 4,270,920 (issued Jun. 2, 1981 to Kondo et al), and U.K. Patent No. 2,052,057 (published Jan. 21, 1981).

In one embodiment, an analytical element comprises a nonporous support having thereon at least one porous spreading zone as the absorbent carrier material. The reducible compound or antibiotic can be in the spreading zone or in a different zone (for example, reagent zone, registration zone or hydrophilic zone). The spreading zone can be prepared from any suitable fibrous or non-fibrous material or mixtures of either or both.

The spreading zone can be prepared using fibrous materials, either mixed with a suitable binder material or woven into a fabric, as described in U.S. Pat. No. 4,292,272 (issued Sept. 29, 1981 to Kitajima et al), from polymeric compositions or particulate materials, with or without binding adhesives, as described in U.S. Pat. Nos. 3,992,158 (issued Nov. 16, 1976 to Przybylowicz et al), 4,258,001 (issued Mar. 24, 1981 to Pierce et al) and 4,430,436 (issued Feb. 7, 1984 to Koyama et al) and Japanese Patent Publication No. 57(1982)-101760 (published Jun. 24, 1982). It is desired that the spreading zones be isotropically porous, meaning that the porosity is the same in each direction in the zone as created by interconnected spaces or pores between particles, fibers or polymeric strands.

Suitable supports can be any suitable dimensionally stable, and preferably, transparent (that is, radiation transmissive) film or sheet material which transmits electromagnetic radiation of a wavelength between about 200 and about 900 nm. A support of choice for a particular element should be compatible with the intended mode of detection (for example, reflection, fluorescence or transmission spectroscopy) and inert to chemical reagents and liquid samples used in the assay. Useful support materials include polystyrene, polyesters, polycarbonates, cellulose esters and others known in the art.

The elements can have a multiplicity of zones which can be superposed layers or distinct areas in the same layer. The reducible compound, polyether antibiotic and any other reagents can be located in the same or different zones within the element. Element configurations are well known in the art, as described, for example in the patents noted above.

A variety of different elements can be prepared in accordance with the present invention. Elements can be configured in a variety of forms, including elongated tapes of any desired width, sheets, slides or chips.

The method carried out with an element can be manual or automated. In general, differentiation is made by taking the element from a supply roll, chip packet or other source and contacting it with a sample (for example, up to 200 µl) of the liquid to be tested so that the sample mixes with the reagents in the element. Such contact can be accomplished in any suitable manner, for example, dipping or immersing the element into the sample or, preferably, by spotting the element by hand or machine with one or more drops of the sample with a suitable dispensing means.

After sample application, the element can be exposed to conditioning, such as incubation, heating or the like, that may be desirable to quicken or otherwise facilitate obtaining any test result. Detection of viable gram-negative microorganisms is achieved when the reducible compound is reduced releasing a species which can be detected in a suitable manner.

Materials used in the following examples were obtained as follows:

gram-negative bacteria *Enterobacter cloacae* (ATCC 23355), *Escherichia coli* (ATCC 25922), *Proteus vulgaris* (ATCC 13315), *Klebsiella pneumoniae* (ATCC 13883) and *Pseudomonas aeruginosa* (ATCC 27853), and gram-positive bacteria *Staphylococcus aureus* (ATCC 25923) and *Streptococcus pyogenes* (ATCC 19615), and brain heart infusion (BHI) broth from Difco Laboratories (Detroit, Mich.),

*Streptococcus faecalis* was isolated from a clinical urine specimen obtained from a local hospital, ionomycin from Behring Diagnostics (La Jolla, Calif.), calimycin (A23187), monensin A, Antibiotic A204, septamycin and lasalocid antibiotics from Eli Lilly Co. (Indianapolis, Ind.), TERGITOL 7 anionic surfactant from Sigma Chemical Co. (St. Louis, Mo.), TRITON X-100 nonionic surfactant from Rohm and Haas (Philadelphia, Pa.), trimethyl-1,4-benzoquinone ETA derived from the corresponding hydroquinone purchased from Aldrich Chemical Co. (Milwaukee, Wis.), and the remainder from Eastman Kodak Co. (Rochester, N.Y.) or prepared using known starting materials and procedures.

In practicing the method of this invention, the following procedures were carried out:

Bacterial suspensions were prepared by growing the cells in BHI to stationary phase overnight at 37° C. *P. aeruginosa* was grown with agitation. About 40 ml of overnight cultures were centrifuged, decanted and washed once with 0.05 molar potassium phosphate buffer or 0.05 molar N-2-hydroxyethylpiperazine-N'-2-ethanesulfonic acid (HEPES) buffer, pH 7.8, and resuspended in buffer.

A dispersion containing a RIND compound was prepared by dissolving RIND VII from Table II above in N,N-dimethylformamide (DMF) at 16 mg compound per ml of solvent. An aliquot (250 µl) of the resulting solution was added to 500 µl of TRITON X-100 surfactant. This mixture was then added dropwise with stirring to 25 ml of 0.05 molar HEPES buffer. A solution containing a water-compatible RIND compound XXXV was prepared by dissolving the compound (16 mg/ml) in N,N-dimethylformamide which had been acidified with a 0.1% sulfuric acid solution.

EXAMPLE 1

Comparative Example

This is an example comparing the method of the present invention with the method of the art described in U.S. Pat. No. 4,525,453, noted above.

TERGITOL 7 anionic surfactant was used to differentiate viable bacteria according to the prior art method. Various concentrations of TERGITOL 7 surfactant were mixed with a 10% glucose solution (50 µl), 3-(4,5-dimethyl-2-thiazolyl)-2,5-diphenyl-2N-tetrazolium bromide (MTT) in methanol (25 µl at 5 mg/ml) or a RIND VII dispersion (1.5 ml) and phenazine methosulfate ETA (25 µl at 3 mg/ml methanol). The volume of each test solution was brought to 3 ml with potassium phosphate buffer. A cell suspension (100 µl at about $10^8$ cells/ml) was then added. The solutions were incubated at 37° C. for 15 and 30 minutes in the presence of either *E. coli*, a gram (−) bacterium, or *S.* aureus, a gram (+) bacterium. The amount of dye formed was then determined visually and graded as follows: 0 indicates no dye formation, +/− indicates faint dye formation, 1+ indicates light dye formation, 2+ indicates moderate dye formation, 3+ indicates strong dye formation, and 4+ indicates very strong dye formation.

The results in Table III below indicate that TERGITOL 7 surfactant provided adequate differentiation when MTT was used as the reducible compound, but it failed to do so when RIND VII was used as the reducible compound.

TABLE III

| TERGITOL 7 Surfactant Concentration | MTT | | | | RIND-VII | | | |
|---|---|---|---|---|---|---|---|---|
| | E. coli (gram −) | | S. aureus (gram +) | | E. coli (gram −) | | S. aureus (gram +) | |
| | 15' | 30' | 15' | 30' | 15' | 30' | 15' | 30' |
| 0 (Control) | 4+ | 4+ | 4+ | 4+ | 4+ | 4+ | 4+ | 4+ |
| 2% (V/V) | 4+ | 4+ | 0 | 0 | +/− | 1+ | 0 | 0 |
| 1.5% | 4+ | 4+ | 0 | 0 | +/− | 1+ | +/− | 1+ |
| 1% | 4+ | 4+ | 0 | 0 | 2+ | 3+ | 1+ | 3+ |
| 0.5% | 4+ | 4+ | 0 | 0 | 3+ | 4+ | 3+ | 4+ |
| 0.2% | 4+ | 4+ | 0 | 0 | 4+ | 4+ | 4+ | 4+ |

Calimycin, a polyether antibiotic, was similarly used with RIND VII in the differentiation of bacteria. Assays were performed as described above, except that 25 μl of 1 molar calcium chloride solution was added to each test solution and the P. aeruginosa response was measured in the presence of 10% yeast extract as the carbon source instead of glucose. The final concentration of calimycin in each test was $10^{-3}$ molar. A control solution containing only calcium chloride did not inhibit reduction of the reducible compound.

The results, given in Table IV below, indicate that calimycin selectively and substantially inhibits the reduction of the reducible compounds by viable gram-positive bacteria, while the reductive capability of the viable gram-negative bacteria is not inhibited.

TABLE IV

| Gram(−) Bacteria | 15 Minutes | 30 Minutes |
|---|---|---|
| E. coli (Control) | 4+ | 4+ |
| E. coli + calimycin | 3+ | 4+ |
| K. pneumoniae (Control) | 4+ | 4+ |
| K. pneumoniae + calimycin | 4+ | 4+ |
| P. vulgaris (Control) | 4+ | 4+ |
| P. vulgaris + calimycin | 4+ | 4+ |
| P. aeruginosa (Control) | 3+ | 4+ |
| P. aeruginosa + calimycin | 2+ | 4+ |

| Gram(+) Bacteria | 15 Minutes | 30 Minutes |
|---|---|---|
| S. aureus (Control) | 4+ | 4+ |
| S. aureus + calimycin | 0 | 0 |
| S. faecalis (Control) | 4+ | 4+ |
| S. faecalis + calimycin | +/− | +/− |
| S. pyogenes (Control) | 4+ | 4+ |
| S. pyogenes + calimycin | 0 | 0 |

EXAMPLES 2–3

Differentiation of Bacteria with Monensin and Lasalocid

These examples demonstrate the use of two polyether antibiotics, monensin and lasalocid, to differentiate between viable gram-positive and gram-negative bacteria in solution assays.

The following materials were used in these examples: stock dispersion of RIND VII as described above, glucose (10% in water), trimethyl-1,4-benzoquinone ETA (1.5 mg/ml methanol), each antibiotic at 1, 5, and 10 mg/ml methanol. Microbial cells were grown as described above. The final approximate cell concentrations were: $1.4 \times 10^7$ cells/ml for E. coli and $2.4 \times 10^7$ cells/ml for S. aureus.

The test solutions were prepared by adding the following, in order: 1.2 ml HEPES, 50 μl glucose solution, 1.5 ml RIND VII dispersion, 100 μl antibiotic solution, 100 μl cell suspension and 25 μl ETA solution. Cell control solutions contained all reagents except antibiotics. Background Controls consisted of both buffer and solution controls. The buffer control contained all reagents except antibiotics and cells. The solution control contained all reagents except cells.

Optical density readings (OD) were made at 635 nm at 0 minutes and after incubation at 37° C. for 30 minutes for all solutions, and the change (ΔOD) was determined. Table V below lists the results expressed as corrected percent inhibition of the reduction of RIND VII. The corrected percent inhibition was calculated by dividing the difference between ΔOD obtained from a Control test without antibiotic and the ΔOD of the test, by the ΔOD of the Control without antibiotic. All readings were corrected by subtracting readings of the appropriate background control. Monensin and lasalocid were effective in differentiating gram-positive and gram-negative bacteria using RIND VII as the reducible compound.

TABLE V

| | Corrected Percent Inhibition | |
|---|---|---|
| | E. coli (gram −) | S. aureus (gram +) |
| Example 2 Lasalocid Concentration | | |
| 0.033 mg/ml | 6.6 | 35.2 |
| 0.166 mg/ml | 10.5 | 50.9 |
| 0.333 mg/ml | 25.5 | 60.1 |
| Example 3 Monensin Concentration | | |
| 0.033 mg/ml | 5.1 | 34.4 |
| 0.166 mg/ml | No inhibition | 43.0 |
| 0.333 mg/ml | No inhibition | 42.0 |

EXAMPLE 4

Differentiation of Bacteria Using a Water-compatible Reducible Compound

This example illustrates differentiation of bacteria according to the present invention using a water-compatible reducible compound and a polyether antibiotic.

A solution was prepared from the following components: 100 μl RIND XXXV solution (16 mg/ml acidified N,N-dimethylformamide), 200 μl glucose solution (10% in water), 200 μl trimethyl-1,4-benzoquinone ETA solution (1.5 mg/ml methanol) and 10 ml HEPES buffer.

Test solutions were prepared from the following reagents: 50 μl HEPES buffer, 50 μl polyether antibiotic A23187 (free acid, 0.01 molar in methanol), 10 μl calcium chloride solution (1 molar) (serial dilutions of buffer and antibiotic were performed to obtain various antibiotic concentrations), 50 μl of the appropriate cell suspensions (*E. coli*, about $10^8$ cells/ml and *S. aureus*, about $10^8$ cells/ml) and 200 μl of the RIND solution. Control solutions were prepared as described in Examples 2 and 3.

Relative fluorescence was measured using a standard spectrophotometer modified to read at excitation of 540 nm and emission of 620 nm. The change (Δ) in relative fluorescence was determined after 30 minutes at 37° C. for several concentration levels of antibiotic. The results are shown in Table VI below. These results show that the composition of the present invention selectively and substantially inhibited the reductive capacity of gram(+) bacteria but not that of the gram(−) bacteria.

TABLE VI

| Antibiotic Concentration (Molar) | Δ Relative Fluorescence after 30 Min. | | |
|---|---|---|---|
| | Solution Control* | E. coli (gram −) | S. aureus (gram +) |
| 0 | 17 | 2539 | 2667 |
| $1 \times 10^{-4}$ | 17 | 2804 | 409 |
| $2 \times 10^{-4}$ | 24 | 2540 | 362 |
| $4 \times 10^{-4}$ | 26 | 2338 | 290 |
| $8 \times 10^{-4}$ | 26 | 2411 | 345 |

*No cells

EXAMPLE 5

Differentiation of Bacteria Using a Tetrazolium Salt

This example illustrates the practice of this invention using a polyether antibiotic and a tetrazolium salt as the reducible compound.

The reducible compound solution was prepared with 3-(4,5-dimethyl-2-thiazolyl)-2,5-diphenyl-2H-tetrazolium bromide (MTT) (200 μl of 5 mg/ml methanol), 200 μl glucose solution (10% in water), 200 μl trimethyl-1,4-benzoquinone ETA (1.5 mg/ml methanol) and 12 ml of HEPES buffer (0.05 molar, pH 7.8).

Test solutions were prepared with the following: 50 μl HEPES buffer, 50 μl polyether antibiotic A23187 (free acid, 0.01 molar in methanol), 10 μl calcium chloride (1 molar) (serial dilutions of buffer and antibiotic were performed to obtain various antibiotic concentrations), 50 μl of the appropriate cell suspension, *E. coli* (about $10^8$ cells/ml) or *S. aureus* (about $10^8$ cells/ml), and 200 μl of the MTT solution. Control solutions were prepared as described in previous Examples.

Optical density measurements were obtained at 540 nm using a standard spectrophotometer and the change in optical density (ΔOD) was determined after 30 minutes at 37° C. The resulting data are shown in Table VII below for several concentrations of antibiotic. It is clear from the data that the composition of this example was useful for differentiating bacteria.

TABLE VII

| Antibiotic Concentration (Molar) | Δ OD after 30 Min. | | |
|---|---|---|---|
| | Solution Control* | E. coli (gram −) | S. aureus (gram +) |
| 0 | 0.065 | 0.643 | 0.505 |
| $1 \times 10^{-4}$ | 0.055 | 0.503 | 0.089 |

TABLE VII-continued

| Antibiotic Concentration (Molar) | Δ OD after 30 Min. | | |
|---|---|---|---|
| | Solution Control* | E. coli (gram −) | S. aureus (gram +) |
| $2 \times 10^{-4}$ | 0.049 | 0.529 | 0.096 |
| $4 \times 10^{-4}$ | 0.079 | 0.512 | 0.065 |
| $8 \times 10^{-4}$ | ** | 0.413 | 0.028 |

*No cells
*Precipitate, no visible color

EXAMPLE 6

Differentiation of Bacteria Using a Dry Analytical Element

This example illustrates the practice of the present invention using a dry analytical element of this invention.

Strips of commercially available 3 mm chromatography paper were washed twice with acetone and immersed in a test solution containing the following: 6 ml methanol, 1 ml RIND XXXV solution (16 mg/ml acidified N,N-dimethylformamide), 1 ml 2,3-dimethoxy-5-methyl-1,4-benzoquinone (1.82 mg/ml methanol), 1 ml glucose solution (10% in water) and 1 ml of polyether antibiotic A23187 (25 mg/ml dimethylsulfoxide). A Control solution was similarly prepared except the antibiotic was omitted. Strips of paper were similarly immersed in the Control solution. All strips were then dried in a dark area at 25° C. for 1 hour.

A standard paper punch was used to cut circular elements (about 0.6 cm in diameter) from the paper strips, and the elements were placed in microtitration plates.

Samples (10 μl) of cell suspensions of *E. coli* (about $5 \times 10^8$ cells/ml) or *S. aureus* (about $5 \times 10^8$ cells/ml) were applied to the elements. Buffer (10 μl) was applied to other elements to measure background. Since polyether antibiotic A23187 requires calcium ions for activity, 25 μl of 1 molar calcium chloride solution was added to 1 ml of each cell suspension or buffer solution prior to application to the elements.

The relative fluorescence (excitation 540 nm, emission 620 nm) was measured using a standard spectrophotometer, and the change in relative fluorescence was determined after 30 minutes at 37° C. Table VIII below shows the results as corrected percent inhibition of the reduction of RIND XXXV, calculated as described in Examples 2 and 3 above. It is apparent that the dry element of this invention is useful for differentiating bacteria.

TABLE VIII

| Bacterium | Corrected Percent Inhibition |
|---|---|
| E. coli (gram −) | 11.5 |
| S. aureus (gram +) | 70 |

EXAMPLE 7

Differentiation of Bacteria Using RIND IX and Ionomycin Polyether Antibiotic

A dispersion of the RIND IX compound was prepared by dissolving the RIND compound in N,N-dimethylformamide (16 mg/ml of solvent acidified with 0.1% concentrated sulfuric acid). An aliquot (250 μl) of the dispersion was added to 500 μl of TRITON X-100 nonionic surfactant. This mixture was then added dropwise with stirring to 25 ml of 0.05 HEPES buffer (pH 7.8).

Test solutions were prepared by adding the following in order: HEPES buffer (1.2 ml), calcium chloride solution (25 μl, 0.1 molar), glucose solution (50 μl, 10% in water), RIND dispersion (1.5 ml), ionomycin (75 μl to give a final concentration of about $1.7 \times 10^{-4}$ molar), 100 μl cells (final concentration of about $10^7$ cells/ml) and trimethyl-1,4-benzoquinone ETA (25 μl, 0.01 molar in methanol). Control solutions were prepared as described in previous Examples. Optical density readings were made at 635 nm and 37° C., and the change in density was determined after 30 minutes. Table IX below lists the results as corrected percent inhibition of the reduction of the RIND compound. This example indicates that the antibiotic ionomycin can be used to differentiate gram-positive and gram-negative bacteria.

TABLE IX

| Bacterium | Corrected Percent Inhibition |
|---|---|
| E. coli (gram −) | No Inhibition |
| S. aureus (gram +) | 59.7 |

EXAMPLES 8 and 9

Differentiation of Bacteria Using RIND XXXV and Antibiotic A204 and Septamycin

These examples are similar to Example 7, but using two other polyether antibiotics, Antibiotic A204 and septamycin. Both antibiotics are useful for differentiation of gram-positive and gram-negative bacteria.

A dispersion of RIND XXXV compound was prepared by adding a solution of the RIND compound (100 μl of 16 mg/ml of acidified N,N-dimethylformamide) and TRITON X-100 nonionic surfactant (200 μl) to a solution of HEPES buffer (9.1 ml), glucose solution (200 μl, 10% in water) and trimethyl-1,4-benzoquinone ETA (200 μl of 1.5 mg/ml of methanol) with stirring.

The antibiotics were premixed with cells as follows: antibiotic solution (50 μl of 10 mg/ml dimethylsulfoxide)) was added to 1 ml of cells ($5 \times 10^7$ cells/ml buffer), and the resulting mixture was allowed to incubate at about 25° C. for 5 minutes. Calcium chloride solution (10 μl, 1 molar) was also added to the solution containing septamycin. Background control solutions contained 1 ml of buffer instead of cells.

Test solution in microtitration wells comprised HEPES (50 μl), antibiotic and cell solution (50 μl) and the RIND dispersion (200 μl). Cell controls did not contain antibiotic.

Relative fluorescence was measured at an emission of 620 nm after excitation at 540 nm using a DYNATECH microfluor Reader, and the change in fluorescence (Δ relative fluorescence) after 30 minutes at 37° C. was determined as the average of two replicates. Table X below shows the results of these tests in terms of corrected percent inhibition as defined in previous examples.

TABLE X

| Antibiotic | Bacterium | Corrected Percent Inhibition |
|---|---|---|
| A204 | E. coli (gram −) | 3.6 |
| | S. aureus (gram +) | 35.8 |
| Septamycin | E. coli (gram −) | 52.3 |
| | S. aureus (gram +) | 74.9 |

The invention has been described in detail with particular reference to preferred embodiments thereof, but it will be understood that variations and modifications can be effected within the spirit and scope of the invention.

We claim:

1. A composition for differentiating between viable gram-positive and gram-negative bacteria comprising:
   (a) a dye or dye precursor capable of being reduced to provide a detectable species by both viable gram-positive and gram-negative bacteria, and
   (b) a polyether antibiotic present in an amount sufficient to selectively and substantially inhibit the reduction of said reducible dye or dye precursor by said gram-positive bacteria.

2. The composition of claim 1 further comprising an electron transfer agent.

3. The composition of claim 1 wherein said antibiotic is selected from the group consisting essentially of calimycin, monensin, antibiotic A204, septamycin, ionomycin and lasalocid.

4. The composition of claim 1 further comprising a cell nutrient containing useful carbon.

5. The composition of claim 1 wherein said reducible dye or dye precursor is represented by the structure CAR—(R$^1$)$_n$ wherein CAR— is a carbocyclic aromatic or quinone nucleus, R$^1$ is a moiety which comprises a shiftable detectable species which is either a chromogen having a first spectral absorption band while attached to said nucleus and a second spectral absorption band when released, or a fluorogen having first spectral absorption and emission bands while attached to said nucleus and second spectral absorption and emission bands when released, and n is 1 or 2,
   provided said reducible dye or dye precursor is capable of being reduced at physiological pH to release said shiftable detectable species, and
   further provided that when R$^1$ is replaced with H, CAR (H)$_n$ has an E$_{\frac{1}{2}}$ of either at least about $+\phi$mV when measured in water, or of at least about $-650$ mV when measured in acetonitrile.

6. The composition of claim 5 wherein said reducible dye precursor has the structure CAR—R$^1$ wherein CAR— is

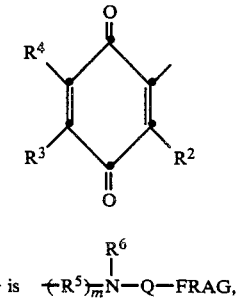

R$^1$ is $+R^5)_{\overline{m}}N-Q-FRAG$,

R$^2$ and R$^4$ are independently hydrogen, alkyl, carbocyclic aryl or an electron withdrawing group having a positive Hammett sigma value, R$^3$ is R$^1$, hydrogen, alkyl, carbocyclic aryl or an electron withdrawing group having a positive Hammett sigma value, provided at least one of R$^2$, R$^3$ and R$^4$ is an electron withdrawing group having a positive Hammett sigma value, or R$^3$ and R$^4$, taken together, represent the atoms necessary to complete a nonaromatic, strained fused carbocyclic 4- to 8-membered ring, $R^5$ is alkylene of 1 or 2 carbon atoms, $R^6$ is alkyl, cycloalkyl, pyridyl, or carbocyclic aryl, Q is carbonyl or thiocarbonyl, FRAG is said shiftable detectable species which provides a detectable species when released from said reducible dye precursor upon reduction by viable bacteria, and m is 0 or 1, provided that when $R^1$ is replaced with H, CAR-H has an $E_{\frac{1}{2}}$ of either at least about +100 mV when measured in water, or of at least about −650 mV when measured in acetonitrile.

7. The composition of claim 6 wherein FRAG provides a chromogen or fluorogen.

8. An analytical element for differentiating between viable gram-positive and gram-negative bacteria comprising an absorbent carrier material and containing:
(a) a dye or dye precursor capable of being reduced to provide a detectable species by both viable gram-positive and gram-negative bacteria, and
(b) a polyether antibiotic present in an amount sufficient to selectively and substantially inhibit the reduction of said reducible dye or dye precursor by said gram-positive bacteria.

9. The element of claim 8 further comprising an electron transfer agent.

10. The element of claim 8 wherein said antibiotic is selected from the group consisting essentially of calimycin, monensin, antibiotic A204, septamycin, ionomycin and lasalocid.

11. The element of claim 8 further comprising a cell nutrient containing useful carbon.

12. The element of claim 8 wherein said reducible dye or dye precursor is represented by the structure CAR—$(R^1)_n$ wherein CAR— is a carbocyclic aromatic or quinone nucleus, $R^1$ is a moiety which comprises a shiftable detectable species which is either a chromogen having a first spectral absorption band while attached to said nucleus and a second spectral absorption band when released, or a fluorogen having first spectral absorption and emission bands while attached to said nucleus and second spectral absorption and emission bands when released, and n is 1 or 2, provided said reducible dye or dye precursor is capable of being reduced at physiological pH to release said shiftable detectable species, and further provided that when $R^1$ is replaced with H, CAR—$(H)_n$ has an $E_{\frac{1}{2}}$ of either at least about +100 mV when measured in water, or of at least about −650 mV when measured in acetonitrile.

13. The element of claim 12 wherein said reducible dye precursor has the structure CAR—$R^1$ wherein CAR— is

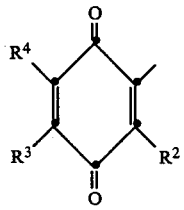

-continued

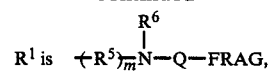

$R^2$ and $R^4$ are independently hydrogen, alkyl, carbocyclic aryl or an electron withdrawing group having a positive Hammett sigma value, $R^3$ is $R^1$, hydrogen, alkyl, carbocyclic aryl or an electron withdrawing group having a positive Hammett sigma value, provided at least one of $R^2$, $R^3$ and $R^4$ is an electron withdrawing group having a positive Hammett sigma value, or $R^3$ and $R^4$, taken together, represent the atoms necessary to complete a nonaromatic, strained fused carbocyclic 4- to 8-membered ring, $R^5$ is alkylene of 1 or 2 carbon atoms, $R^6$ is alkyl, cycloalkyl, pyridyl, or carbocyclic aryl, Q is carbonyl or thiocarbonyl, FRAG is said shiftable detectable species which provides a detectable species when released from said reducible dye precursor upon reduction by viable bacteria, and m is 0 or 1, provided that when $R^1$ is replaced with H, CAR—H has an $E_{\frac{1}{2}}$ of either at least about +100 mV when measured in water, or of at least about −650 mV when measured in acetonitrile.

14. A method for differentiating between viable gram-positive and gram-negative bacteria comprising the steps of:
A. mixing a first sample of a liquid suspected of containing viable gram-positive or gram-negative bacteria with a dye or dye precursor capable of being reduced to provide a detectable species by both viable gram-positive and gram-negative bacteria,
B. mixing a second sample of said liquid with
(a) said dye or dye precursor, and
(b) a polyether antibiotic present in an amount sufficient to selectively and substantially inhibit the reduction of said reducible dye or dye precursor by said gram-positive bacteria, and
C. measuring the difference between detectable species resulting from steps A and B.

15. The method of claim 14 wherein said liquid is also mixed with an electron transfer agent and a cell nutrient containing useful carbon.

16. The method of claim 14 wherein said antibiotic is selected from the group consisting essentially of calimycin, monensin, antibiotic A204, septamycin, ionomycin and lasalocid.

17. The method of claim 14 wherein said detectable species is determined colorimetrically or fluorometrically.

18. The method of claim 14 wherein said reducible dye or dye precursor is represented by the structure CAR—$(R^1)_n$ wherein CAR— is a carbocyclic aromatic or quinone nucleus, $R^1$ is a moiety which comprises a shiftable detectable species which is either a chromogen having a first spectral absorption band while attached to said nucleus and a second spectral absorption band when released, or a fluorogen having first spectral absorption and emission bands while attached to said nucleus and second spectral absorption and emission bands when released, and n is 1 or 2, provided said reducible dye or dye precursor is capable of being reduced at physiological pH to release said shiftable detectable species, and further provided that when $R^1$ is replaced with H, CAR–(H)$_n$ has an $E_{\frac{1}{2}}$ of either at least about $+100$ mV when measured in water, or of at least about $-650$ mV when measured in acetonitrile.

19. The method of claim 18 wherein said reducible dye precursor has the structure CAR—$R^1$ wherein CAR— is

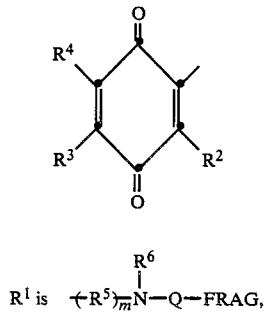

$R^1$ is $-(R^5)_{\overline{m}}N-Q-FRAG$, $R^2$ and $R^4$ are independently hydrogen, alkyl, carbocyclic aryl or an electron withdrawing group having a positive Hammett sigma value, $R^3$ is $R^1$, hydrogen, alkyl, carbocyclic aryl or an electron withdrawing group having a positive Hammett sigma value, provided at least one of $R^2$, $R^3$ and $R^4$ is an electron withdrawing group having a positive Hammett sigma value, or $R^3$ and $R^4$, taken together, represent the atoms necessary to complete a nonaromatic, strained fused carbocyclic 4- to 8-membered ring, $R^5$ is alkylene of 1 or 2 carbon atoms, $R^6$ is alkyl, cycloalkyl, pyridyl, or carbocyclic aryl, Q is carbonyl or thiocarbonyl, FRAG is said shiftable detectable species which provides a detectable species when released from said reducible dye precursor upon reduction by viable bacteria, and m is 0 or 1, provided that when $R^1$ is replaced with H, CAR—H has an $E_{\frac{1}{2}}$ of either at least about $+100$ mV when measured in water, or of at least about $-650$ mV when measured in acetonitrile.

20. The method of claim 14 for the differentiation of viable human urinary tract gram-positive and gram-negative bacteria.

* * * * *